United States Patent [19]
Clubb et al.

[11] Patent Number: 5,815,904
[45] Date of Patent: Oct. 6, 1998

[54] METHOD FOR MAKING A STENT

[75] Inventors: Thomas L. Clubb, Hudson, Wis.;
James V. Donadio, III, Chaska, Minn.;
Mark O. Dustrude, Minnetonka,
Minn.; J. Edward Shapland, II,
Shoreview, Minn.

[73] Assignee: IntraTherapeutics, Inc., St. Paul, Minn.

[21] Appl. No.: 816,666

[22] Filed: Mar. 13, 1997

[51] Int. Cl.⁶ ........................................ B23P 17/00
[52] U.S. Cl. .................... 29/418; 29/445; 623/1; 623/12; 228/159; 606/198
[58] Field of Search .............. 29/418, 445, 525.01, 29/525.14, 557; 606/194, 195, 198; 623/1, 12; 228/159, 161, 193

[56] References Cited

U.S. PATENT DOCUMENTS

| | | | |
|---|---|---|---|
| 4,434,546 | 3/1984 | Hershberger | 29/418 |
| 4,610,068 | 9/1986 | Schultz | 29/418 |
| 4,866,826 | 9/1989 | Koide | 29/445 |
| 5,195,984 | 3/1993 | Schatz | 623/1 |
| 5,354,309 | 10/1994 | Schnepp-Pesch et al. | 623/1 |
| 5,693,085 | 12/1997 | Buirge et al. | 623/1 |
| 5,713,949 | 2/1998 | Jayaraman | 606/198 |
| 5,733,303 | 3/1998 | Israel et al. | 623/12 |

*Primary Examiner*—David P. Bryant
*Attorney, Agent, or Firm*—Merchant, Gould, Smith, Edell, Welter & Schmidt

[57] ABSTRACT

The present invention relates to a method for manufacturing a tubular medical device for insertion in a body. The method includes the step cutting a plurality of cross-sectional pieces or layers from a flat sheet. The pieces are cut so as to define inner apertures. The pieces are then aligned generally along an axis such that the pieces are arranged to form an elongated structure having an interior lumen extending longitudinally therethrough. Finally, the aligned pieces of the elongated structure are connected together such that each interconnected piece forms a layer of the tubular medical device.

23 Claims, 9 Drawing Sheets

FIG. 1B
FIG. 1C
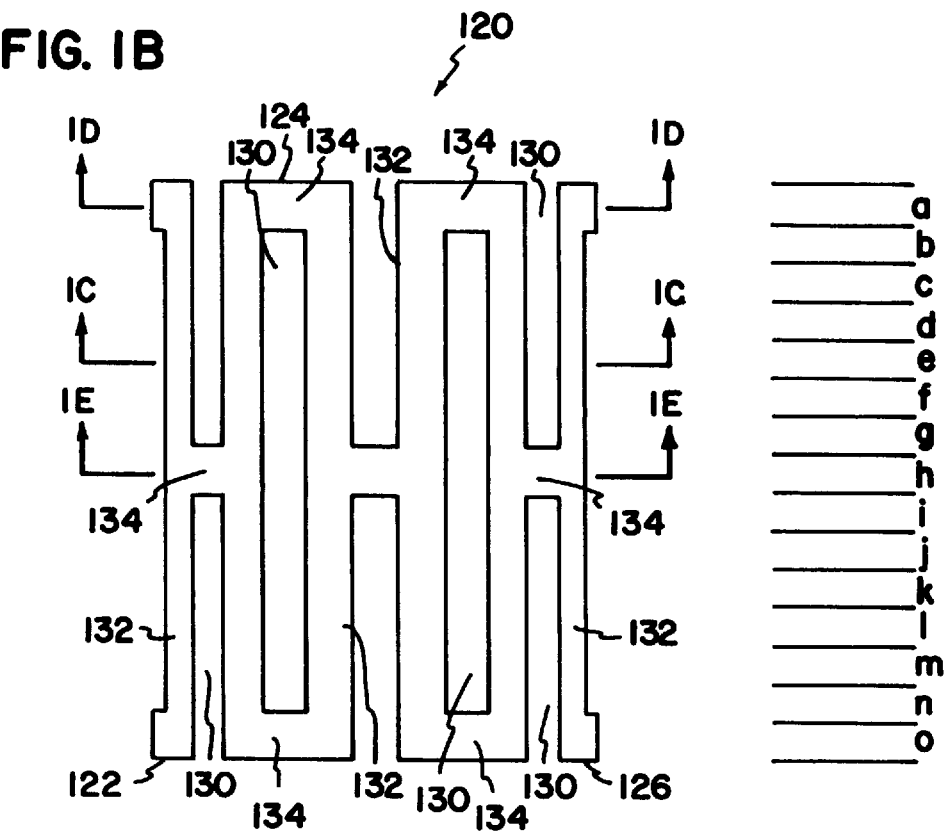
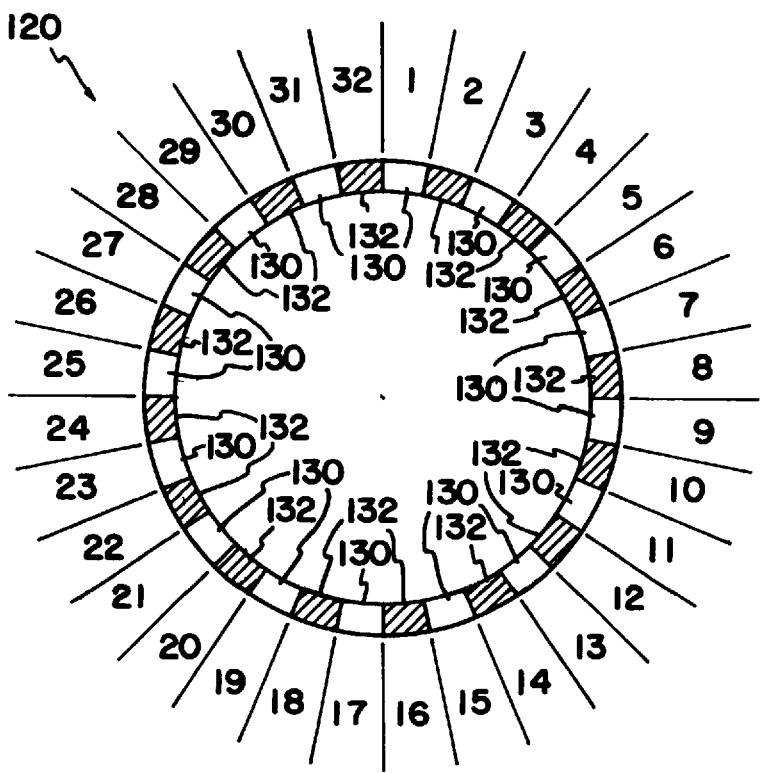

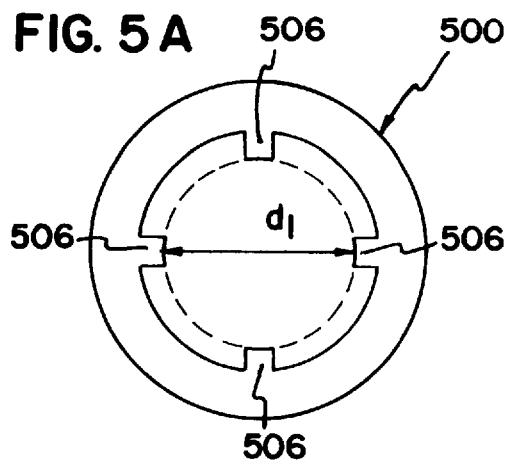
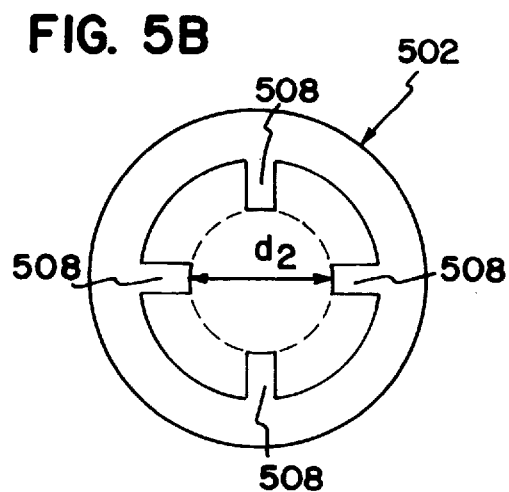
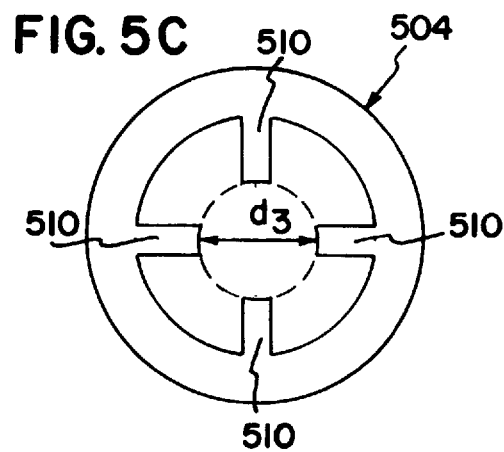

METHOD FOR MAKING A STENT

FIELD OF THE INVENTION

The present invention relates generally to a method for making a tube-like structure defining a plurality of apertures. More particularly, the present invention relates to a method for making an intraluminal medical device such as a stent.

BACKGROUND OF THE INVENTION

Stents are commonly used to provide mechanical reinforcement for maintaining the patency of body passageways and cavities. Exemplary body passageways include blood vessels, the urethra, the bile duct, the esophagus, and the ureters.

A common use for stents is in the treatment of coronary artery disease. Coronary artery disease involves the narrowing or constricting of a coronary artery such that blood flow through the artery is diminished. Such a situation is commonly treated by balloon angioplasty procedures in which the afflicted artery is dilated/expanded through the use of a balloon catheter. Without artificial reinforcement, the balloon expanded vessel has a tendency to constrict back to its previous obstructed internal diameter shortly after an angioplasty procedure. By implanting a stent along the expanded portion of the vessel, the vessel is provided with sufficient radial reinforcement to prevent the vessel from constricting.

Besides preventing vessel constriction, stents provide another function when used in association with balloon angioplasty procedures. During a typical balloon angioplasty procedure, it is common for the afflicted artery to split or tear as it is expanded. The tearing of the vessel produces flaps of tissue that may project into the lumen of the vessel thereby interfering with blood flow. To prevent the aforementioned problem, a stent is implanted at the obstruction/constriction location. The stent compresses the flaps against the vessel to prevent interference with blood flow and to prevent the flaps from tearing from the vessel and entering the blood stream.

A variety of techniques exists for manufacturing stents. One technique involves forming wire members about a cylindrical support member such as a mandrel. The wire members are wrapped about the mandrel so as to overlap or intertwine with one another. The wire members are preferably interconnected at the intersection points between the wire members by conventional techniques such as welding, blazing or soldering. Once the wire members are suitably interconnected, the mandrel is removed from the wire members thereby leaving an elongated wire mesh tube having a plurality of openings defined between the individual wire members.

Another manufacturing technique commonly employed to manufacture stents involves initially providing a thin-walled stainless steel tube. Initially, the wall of the tube is solid. A pattern of openings is then cut into the solid wall of the tube by such techniques such as electromechanical or laser etching.

One concern in the stent manufacturing industry is high manufacturing cost. Another concern relates to the ability to manufacture reliable, strong stents having improved fluid flow characteristics. A further concern in this area relates to the ability to manufacture stents having asymmetrical configurations. There is a need in the art for stent manufacturing methods which address these concerns and other concerns.

SUMMARY OF THE INVENTION

The present invention relates generally to a method for manufacturing a tubular medical device for insertion in a body. The method includes the step of providing a sheet of biocompatible material. Next, a plurality of pieces are cut from the sheet. The pieces are preferably annular and preferably defining central apertures. Once the pieces are cut from the sheet, the pieces are aligned generally along an axis such that the pieces are arranged to form an elongated structure having an interior lumen extending longitudinally therethrough. The aligned pieces of the elongated structure are then connected together such that each of the interconnected pieces forms a layer of the elongated tubular medical device.

In certain embodiments of the present invention, the pieces are connected by diffusion bonding. In other embodiments, the pieces are connected by a connecting member that extends longitudinally through the elongated structure to interconnect the pieces. In still other embodiments of the present invention, the pieces include inner or outer radial projections. In such embodiments, inner or outer portions of the elongated structure are removed such that the radial projections are left as a remainder of the elongated structure. Such remaining radial projections are configured to form an elongated tubular medical device having a plurality of lateral openings.

The present invention provides a manufacturing technique that allows stents or other tubular medical devices to be made utilizing manufacturing techniques commonly used to manufacture flat structures. Manufacturing techniques employed to manufacture flat structures are readily conducive to automation and can be used to rapidly mass produce articles at a low cost. Consequently, the present invention provides a manufacturing technique suitable for reducing stent manufacturing costs.

The present invention also provides a manufacturing technique suitable for making tubular medical devices having asymmetrical configurations. By varying the structure of a given stent at predetermined locations, stents can be manufactured having physical characteristics, such as strength and flexibility, which vary along the length of the stent. For example, the cross-sectional area of a given stent strut can be increased at certain locations to increase rigidity and strength at such locations. By contrast, the cross-sectional area of a given stent strut can be decreased at certain locations to increase flexibility at such locations. Additionally, the internal diameter of a given tubular medical device can be varied to achieve desired flow characteristics within the tubular device.

A variety of additional advantages of the invention will be set forth in part in the description which follows, and in part will be obvious from the description, or may be learned by practice of the invention. The advantages of the invention will be realized and attained by means of the elements and combinations particularly pointed out in the claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. A brief description of the drawings is as follows:

FIG. 1B is a front view of the stent of FIG. 1A that defines multiple cross-sectional layers of the stent;

FIG. 1C is a cross-sectional view of the stent of FIG. 1B taken along section line 1C—1C;

FIGS. 5A—5C illustrate alternative cross-sectional pieces suitable for making a tubular medical device having an internal diameter that varies along the length of the device;

DETAILED DESCRIPTION OF AN EXEMPLARY EMBODIMENT

Reference will now be made in detail to exemplary embodiments of the present invention which are illustrated in the accompanying drawings. Wherever possible, the same reference numbers will be used throughout the drawings to refer to the same or like parts.

Figure 1A:
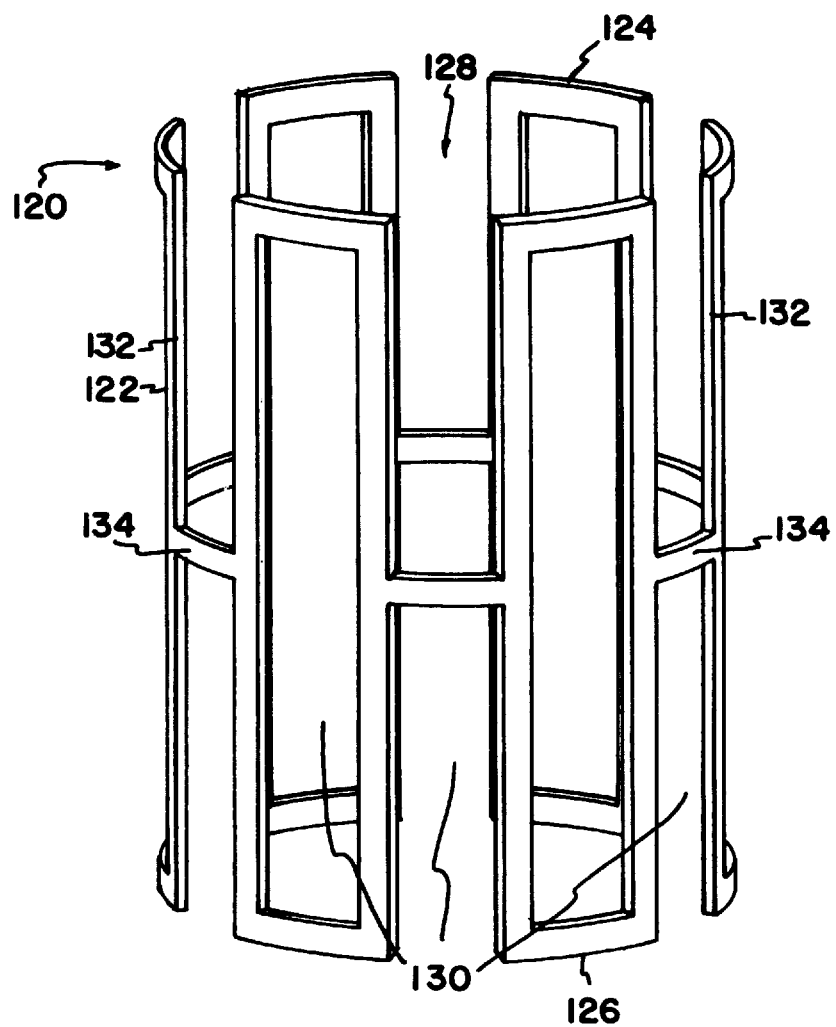
FIG. 1A is a perspective view of an exemplary stent.

FIG. 1A shows an exemplary stent 120 that can be manufactured utilizing the principles of the present invention. It will be appreciated that the stent 120 is but one example of many stents that can be manufactured using the general principles of the present invention. For the purpose of clearly explaining the principles of the present invention, the stent 120 has a relatively simple and consistent pattern of openings. However, it will be appreciated that the methods within the broad scope of the present invention can be utilized to manufacture stents or other tubular structures having a variety of opening patterns of wide ranging complexity. Additionally, the stent 120 is shown having struts with substantially rectangular cross-sections. It will be appreciated that by practicing the present invention, stents with struts having various cross-sectional shapes can be manufactured. Exemplary cross-sectional shapes include rounded shapes, curved shapes, asymmetrical shapes, hourglass shapes, elliptical shapes, triangular shapes, or any other type of polygonal shapes.

The stent 120 comprises a generally tubular body 122 having a first end 124 opposite a second end 126. A central opening 128 extends longitudinally between the first and second ends 124 and 126 of the body 122. A plurality of generally rectangular side openings 130 extend transversely through the body 122. The rectangular side openings 130 are defined by a plurality of longitudinal struts 132 that are interconnected by a plurality of transverse struts 134. The longitudinal struts 132 and the transverse struts 134 together comprise the body 122 of the stent 120.

FIG. 1B shows a front view of the stent 120. As shown in FIG. 1B, the stent 120 is divided into fifteen vertically stacked cross-sectional layers which have been assigned reference letters a–o. To facilitate explaining the present invention, the thickness or height of each transverse strut 134 has been selected so as to equal to the thickness of each of the defined fifteen layers.

FIG. 1C is a cross-sectional view of the stent 120 taken along section line 1C—1C. It will be appreciated that the cross-sectional view of FIG. 1C is representative of layers b–g and i–n. For the purpose of explanation, the stent 120 has been divided into thirty-two evenly-spaced radial positions or sections which have been assigned reference numerals 1–32. To simplify the explanation of the present manufacturing method, the width of each radial position is generally equal to the thickness of each lateral opening 130 and the width of each of the longitudinal strut members 132. As shown in FIG. 1C, each of the even radial positions is occupied by one of the longitudinal struts 132.

Figure 1D:
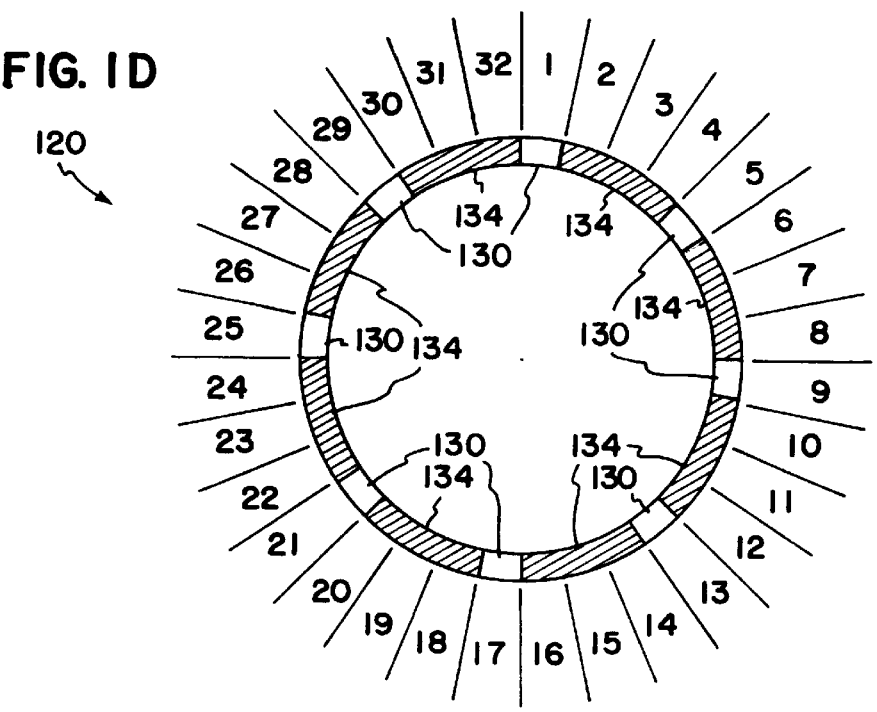
FIG. 1D is a cross-sectional view of the stent of FIG. 1B taken along section line 1D—1D.

FIG. 1D provides another cross-sectional view of the stent 120. The cross-sectional view of FIG. 1D is representative of layers a and o of the stent 120. As shown in FIG. 1D, the stent 120 has been divided into the same thirty-two evenly spaced radial positions previously described with respect to FIG. 1C. In layers a and o, the transverse struts 134 are configured to occupy radial positions 2–4, 6–8, 10–12, 14–16, 18–20, 22–24, 26–28, and 30–32.

Figure 1E:
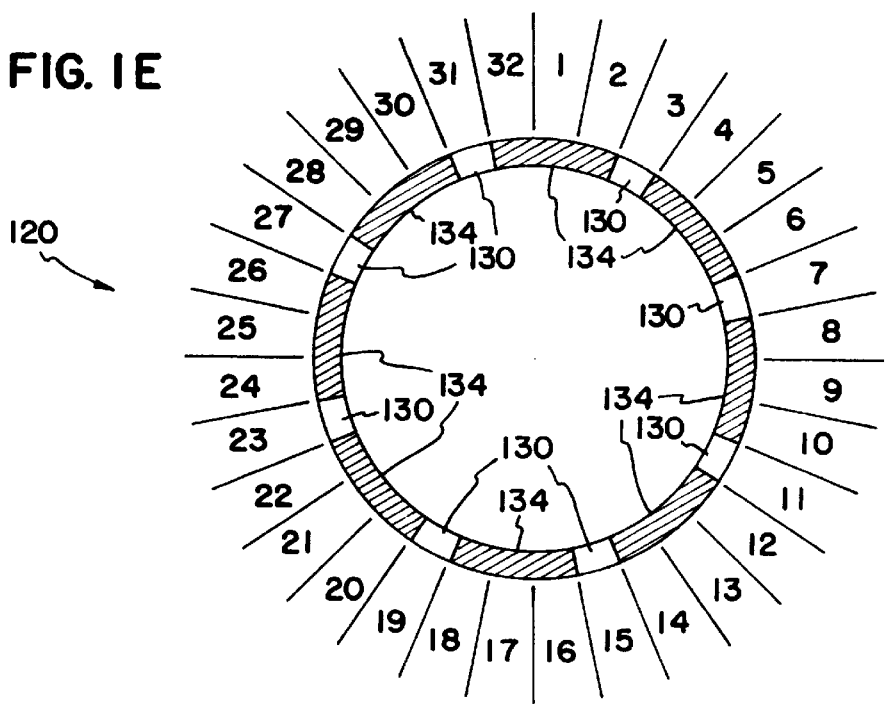
FIG. 1E is a cross-sectional view of the stent of FIG. 1B taken along section line 1E—1E.

FIG. 1E shows a further cross-sectional view of the stent 120. The cross-sectional view of FIG. 1e is representative of layer h of the stent 120. Once again, the cross-sectional view shows the stent 120 divided into the same thirty-two equal radial positions. It will be appreciated that layer h of the stent 120 has substantially the same cross-sectional configuration as layers a and o of the stent 120. However, the transverse strut configuration of layer h has been rotated clockwise by two radial positions relative to the layers a and o. For example, as shown in FIG. 1e, the transverse struts 134 of layer h are configured to occupy radial positions 4–6, 8–10, 12–14, 16–18, 20–22, 24–26, 28–30, and 32–2. As a result of the shifting of the transverse struts 134, the transverse struts 134 of layer h are staggered with respect to the transverse struts of the layers a and o.

The present invention relates generally to a method for manufacturing tube-like structures by cutting cross-sectional pieces from a flat sheet of material and then connecting the pieces together so they form individual cross-sectional layers of an elongated tube-like structure. It will be appreciated that the manufacturing technique of the present invention can be used to manufacture tube-like structures having varying configurations. Throughout the specification the various methods are described as being methods for manufacturing stents. However, it will be appreciated that the same methods are applicable for manufacturing a variety of other tubular medical devices configured to be inserted in a human body.

An exemplary method for manufacturing the specific stent embodiment shown in FIG. 1a–1e involves cutting each of the fifteen cross-sectional layers of the stent 120 from flat sheets of biocompatible material and then connecting the pieces together to form an elongated tube member. The sheets preferably each have a thickness equal to the desired thickness of each cross-sectional layer of the stent 120. It will be appreciated that the sheets of biocompatible material may be made from a wide range of materials. Exemplary biocompatible materials include silver, tantalum, stainless steel, gold, titanium, nitinol, or any suitable plastic material. It will also be appreciated that the individual cross-sectional layers can be cut from the sheets of biocompatible material by a variety of cutting processes. Exemplary cutting techniques include stamping, electromechanical cutting, laser cutting, and chemical etching.

Figure 2A:
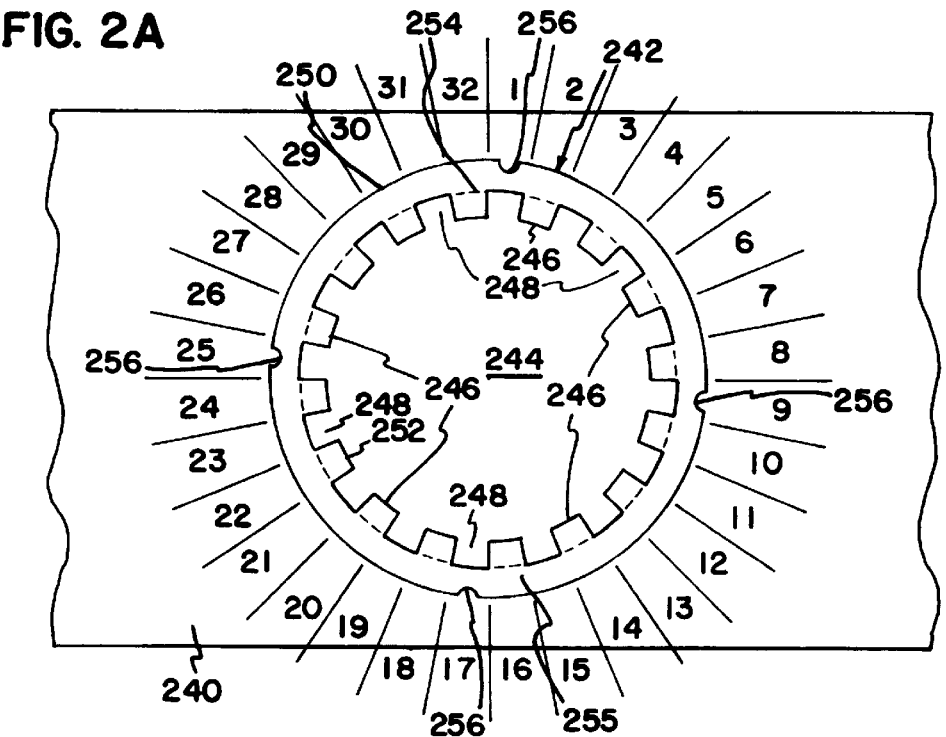
FIG. 2A shows a sheet of material having an exemplary cross-sectional piece or layer of a stent cut therein.

FIG. 2A shows an exemplary sheet 240 of biocompatible material. To manufacture the stent 120 of FIGS. 1A–1E, twelve first cross-sectional pieces 242 or washer structures are cut from the sheet 240 (only one of the first pieces 242 is shown in FIG. 2A). The first pieces 242 are used to manufacture layers b–g and i–n of the stent 120. Each of the cross-sectional pieces 242 defines a generally circular central aperture 244 and includes radial portions 246 extending radially into the aperture 244. The radial portions 246 are spaced circumferentially about the aperture 244 and define void spaces 248 located radially between each of the radial portions 246.

Each first cross-sectional piece 242 also includes a circular exterior boundary 250, a circular interior boundary 252, and a circular intermediate boundary 254 positioned between the interior and exterior boundaries 252 and 250. Each of the boundaries 250, 252 and 254 are preferably concentrically aligned. In each first piece 242, the radial portions 246 are preferably positioned between the interior boundary 252, which is defined by the interior sides of the radial portions 246, and the intermediate boundary 254 which is located where the radial portions 246 merge with the main body of the piece 242. An annular substantially solid exterior portion 255 is defined between each intermediate boundary 254 and each exterior boundary 250. Keyway notches or slots 256 are located at predetermined locations about the circumference of each exterior portion 255. Specifically, with respect to the first cross-sectional pieces 242, the keyway notches 256 are individually located adjacent to the first, ninth, seventeenth, and twenty-fifth radial positions.

It will be appreciated that the radial portions 246 positioned inside of each intermediate boundary 254 have a configuration that is substantially the same as the cross-sectional configuration of layers b–g and i–n of the stent 120.

Figure 2B:
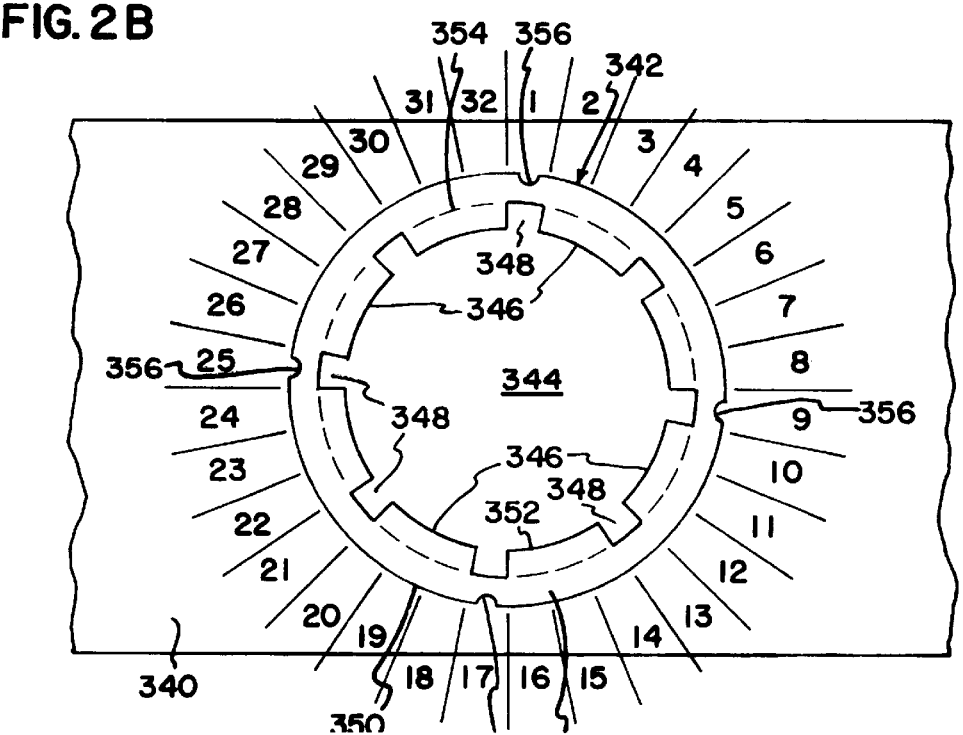
FIG. 2B shows sheet of material having another cross-sectional piece or layer of a stent cut therein.
Figure 2C:
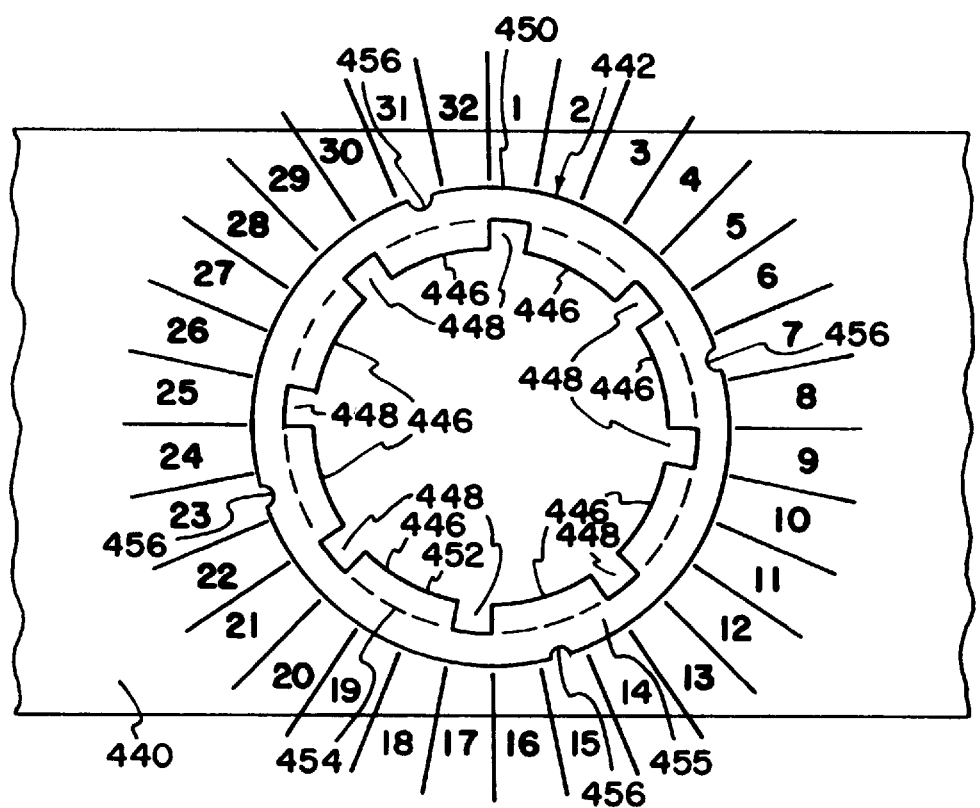
FIG. 2C shows a sheet of material having a further cross-sectional piece or layer of a stent cut herein.

FIG. 2B shows another sheet 340 of biocompatible material. To manufacture the stent 120, two second cross-sectional pieces 342 are cut from the sheet 340 (only one of the cross-sectional pieces is shown in FIG. 2C). The second pieces 342 are configured to make layers a and o of the stent 120. Each of the second cross-sectional pieces 342 has a generally angular shapes and defines a central aperture 344. The second pieces 342 also include radial members 346 that extend radially into the apertures 344 and that are spaced about the circumference of the aperture 344. Void spaces 348 are located between the radial members 346. Each of the second cross-sectional pieces 342 also includes a circular outer boundary 350, a circular inner boundary 352 defined by inner edges of radial members 346, and an intermediate boundary 354 positioned between the interior and exterior boundaries 352 and 350. The radial members or portions 346 are positioned between the inner boundary 352 and the intermediate boundary 350. It will be appreciated that the radial portions 346 positioned inside of each intermediate boundary 354 have a configuration that is substantially the same as the cross-sectional configuration of layers a and o of the stent 120.

A solid annular exterior portion 355 is located between the exterior and intermediate boundaries 350 and 354. A plurality of keyways or notches 356 are formed about the circumference of the exterior portion 355. For example, as shown in FIG. 2B, the notches 356 are radially aligned with the first, ninth, seventeenth, and twenty-fifth radial positions of the second cross-sectional pieces 342.

FIG. 2C shows a sheet 440 of biocompatible material having a third cross-sectional piece 442 cut therein. The third cross-sectional piece 442 is configured to make or form layer h of the stent 120. The third cross-sectional piece 442 has a generally annular shape and defines a generally circular interior aperture 444. Radial members 446 project radially into the aperture 440 from the main body of the third piece 442. The radial members 442 are uniformly spaced about a circumference of the aperture 444. Slots or void openings 448 are defined radially between each of the individual radial members 446.

The third cross-sectional piece 442 includes a circular exterior boundary 450, a circular interior boundary 452, and an intermediate boundary 454 positioned between the exterior and interior boundaries 450 and 452. The interior boundary 452 is defined by inner edges of the radial members 446. The intermediate boundary 454 is aligned along the region where the radial members 446 intersect with or connect to the main body of the third cross-sectional piece 442. The radial members 442 are positioned between the interior boundary 452 and the intermediate boundary 454. An exterior portion 455 of the third cross-sectional piece 442 is located between the intermediate boundary 454 and the exterior boundary 450. A plurality of keyways or notches 456 are spaced about the circumference of the exterior portion 455. The notches 456 are shown aligned with the seventh, fifteenth, twenty-third, and thirty-second radial positions of the third cross-sectional piece 442.

It will be appreciated that the third cross-sectional piece 442 has substantially the same configuration as the second cross-sectional piece 342. However, the one substantial differences between the second and third cross-sectional pieces 342 and 442 relates to the relative positioning of the keyways 356 and 456. Specifically, the keyways 456 of the third cross-sectional piece 442 have been rotated counter-clockwise two radial positions relative to the keyways 356 of the second cross-sectional pieces 342.

Figure 3A:
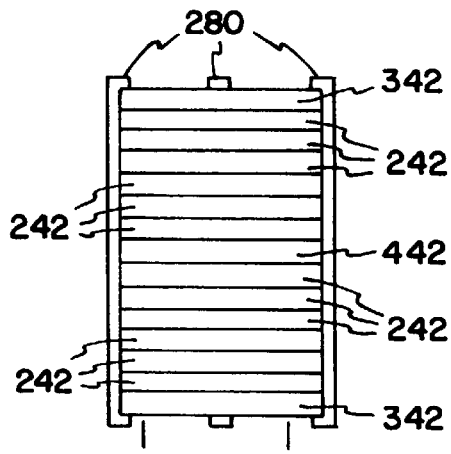
FIG. 3A is a front view illustrating a plurality of cross-sectional pieces stacked on a support structure so as to form an elongated tube structure.
Figure 3B:
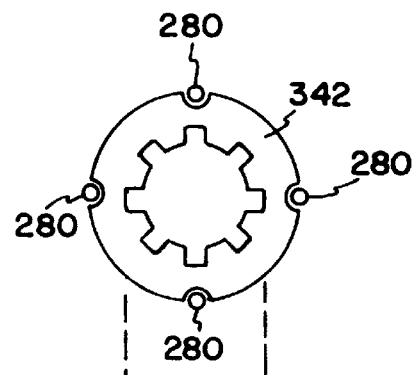
FIG. 3B is a top view of the tube structure of FIG. 3A.

After the cross-sectional pieces 242, 342 and 442 have been cut from their respective sheets of biocompatible material, the cross-sectional pieces 242, 342, and 442 are aligned or stacked so as to form an elongated tube structure defining a longitudinal opening extending throughout its length. FIGS. 3A and 3B show the cross-sectional pieces 242, 342 and 442 aligned within a support structure. As shown in FIGS. 3A and 3B, the support structure includes four alignment members or posts 280 spaced about an outer circumference defined by the aligned cross-sectional pieces 242, 342 and 442. The posts 280 have diameters slightly smaller than the size of the keyway notches 256, 356 and 456. The posts are fit within the keyways of the cross-sectional pieces 242, 342 and 442 to maintain the pieces in the aligned configuration. The posts 281 also function to maintain a predetermined relative radial orientation between each of the individual cross-sectional pieces 242, 342 and 442. For example, the third piece 442 is shifted two radial positions relative to the second pieces 342

In the aligned configuration, the individual intermediate boundaries of the cross-sectional pieces 242, 342 and 442 cooperate to form an elongated cylindrical intermediate boundary of the elongated member. Similarly, the individual interior boundaries of the cross-sectional pieces 242, 342 and 442 cooperate to form an elongated cylindrical internal boundary of the elongated member. Finally, the individual exterior boundaries of the cross-sectional pieces 242, 342 and 442 cooperate to define an elongated cylindrical exterior boundary of the tube member.

Once the cross-sectional pieces 242, 342 and 442 have been arranged in the predetermined configuration, the pieces 242, 342 and 442 are connected together. Preferably, the individual cross-sectional pieces 242, 342 and 442 are fused together such that the elongated tube comprises a one-piece unit. For example, the pieces can be connected by techniques such as diffusion bonding, adhesive bonding, laser welding, and brazing. Additionally, an connecting member may extend through at least one radial member of each cross-sectional piece to connect the individual pieces together.

Figure 4A:
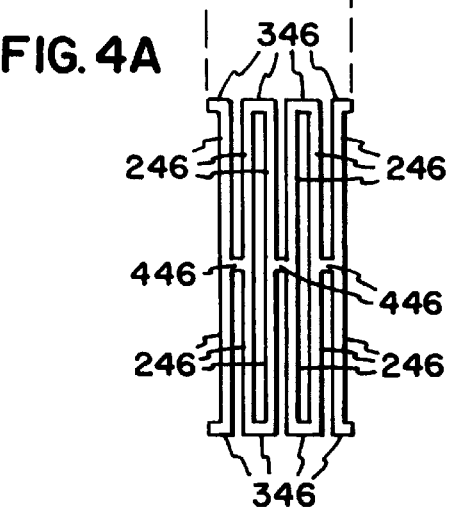
FIG. 4A is a front view of a stent structure formed by removing an exterior portion of the elongated tube of FIG. 3A.
Figure 4B:
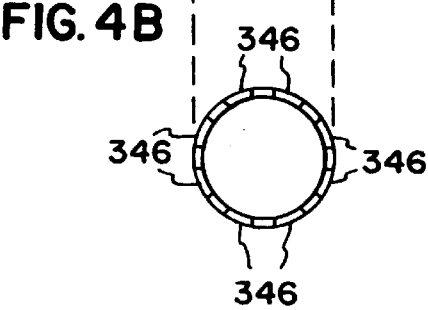
FIG. 4B is a top view of the stent of FIG. 4A.

After the individual cross-sectional pieces 242, 342 and 442 have been interconnected, the elongated tube is removed from the support structure and the exterior portions 255, 355 and 455 of the cross-sectional pieces 242, 342 and 442 are removed from the elongated member by conventional techniques such as a conventional machining process. FIGS. 4A and 4B show the resultant structure after the exterior portions 255, 355 and 455 have been removed. It will be appreciated that once the exterior portions 255, 355 and 455 are removed, only the radial portions 246, 346 and 446 of the cross-sectional pieces 42, 142 and 242 remain. The remaining radial portions 246, 346 and 446 are preferably fused together and form a body of a stent having an outer diameter contiguous with the intermediate boundary of the elongate member and an inner diameter contiguous with the interior boundary of the elongated member. The void spaces 244, 344 and 444 between the radial portions 246, 346 and 446 form transverse openings in the stent body.

It will be appreciated that the resulting stent body has exactly the same configuration as the stent 120 illustrated in FIGS. 1a–1e. The void spaces 248, 348 and 448 cooperate to form the transverse openings 130 in the stent 120. Additionally, the radial portions 246 of the twelve first pieces 242 form the longitudinal struts 132 of the stent 120. Furthermore, the radial portions 346 of the two second pieces 342, and the radial portions 446 of the single third piece 442, form the transverse struts 134 of the stent 120.

FIGS. 5A–5C illustrate alternative first, second, and third substantially flat annular pieces 500, 502, and 504 or washers. The first piece 500 defines a plurality of first inner radial projections 506 having inner edges that define a first inner diameter $d_1$. The second piece 502 defines a plurality of second inner radial projections 508 that define a second inner diameter $d_2$. The second projections 508 project further inward than the first projections 506. Consequently, the second inner diameter $d_2$ is smaller than the first inner diameter $d_1$. The third piece 504 defines a plurality of third inner radial projections 510 that define a third inner diameter $d_3$. The third projections 510 project further inward than the second projections 508. Consequently, the third inner diameter $d_3$ is smaller than the second inner diameter $d_2$.

In practicing a method in accordance with the principles of the present invention, the pieces 500, 502, and 504 are cut from a substantially flat section of biocompatible material. Then, as previously described with respect to the method shown by FIGS. 3A–4B, the pieces 500, 502, and 504, along with other pieces, are aligned or stacked on a support device to form a tubular structure.

The pieces 500, 502, and 504 form a portion of the tubular structure that has a tapered inner diameter defined by the inner edges of the radial projections 506, 508, and 510. For the purpose of illustration, there is a substantial inner diameter variation between each of the pieces 500, 502, and 504. In practice, the inner diameter variation between consecutive stacked pieces is gradual so as to provide a small inner diameter variation having desirable fluid flow characteristics.

Once the pieces of the tube structure have been aligned, the pieces are connected together by exemplary techniques such as diffusion bonding, brazing, adhesive bonding and laser welding. Next, an exterior portion of the tube structure is removed such that only the inner radial projections of the pieces remain. The remaining inner radial portions 506, 508, and 510 form longitudinal struts of a stent. Such longitudinal struts have cross-sectional areas which vary along the lengths of the struts. The inner edges of the struts define an inner stent diameter which tapers along the length of the stent.

As shown in FIGS. 5A–5C, each of the inner radial projections of a given annular piece has the same cross-sectional configuration. In alternative embodiments, selected inner radial projections of a given annular piece can have cross-sectional areas that are either larger or smaller than the remainder of the radial projection of the piece. In practicing the present invention, such pieces can be used to manufacture stents having asymmetrical configurations. For example, a stent having a single strut that is thicker and more rigid than the remainder of the struts can be manufactured. Additionally, a stent having a single strut having a cross-section area than varies can be manufactured. Of course, the present invention is not limited to manufacturing stents with single struts that vary in cross-sectional area with respect to the remaining struts. In fact, the present invention allows each strut or cross-member of a stent to be manufactures with a unique cross sectional area and shape. By varying the size and shape of selected struts and cross-members at predetermined locations on the stent, the stent can be designed having regions with varying flexibility and strength.

Figure 6:
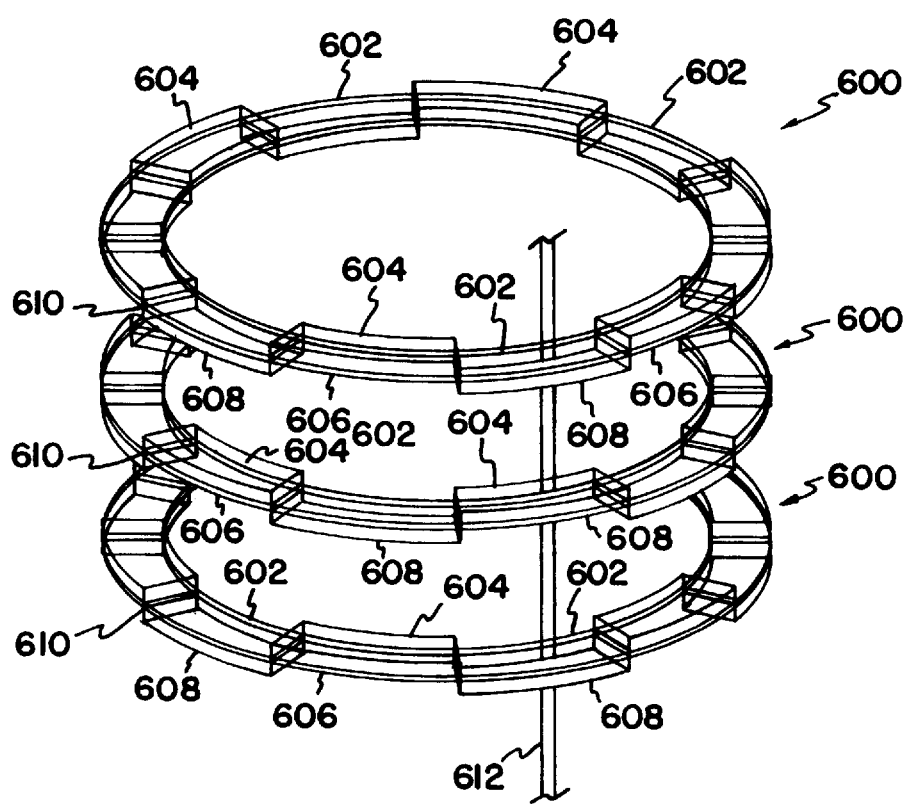
FIG. 6 shows an alternative method in accordance with the principles of the present invention for manufacturing tubular medical devices.

FIG. 6 shows alternative annular pieces 600 or washers suitable for use in accordance with the principles of the present invention. Each piece 600 includes generally rectangular top recesses 602 defined between generally rectangular top projections 604. Each piece 600 also includes generally rectangular bottom recesses 606 defined between generally rectangular bottom projections 608. The recesses 602, 606 and the projections 604, 608 are uniformly spaced about the circumference of each piece 600. A continuous central portion or layer 610 extends throughout each piece 600 between the top and bottom projections 604 and 608.

In practicing a method in accordance with the principles of the present invention, the pieces 600 are cut, preferably by an etching technique, from a substantially flat sheet of biocompatible material. Once the pieces 600 have been cut, the pieces 600 are aligned or stacked on a support structure so as to form a tubular structure. As shown in FIG. 6, the pieces 600 are aligned so that the bottom projections 608 of a top piece align with the top projections 604 of a piece positioned directly below the top piece. Once the pieces 600 are aligned to from the tube structure, the pieces 600 are connected together. For example, the pieces 600 can be fused together. Alternatively, as shown in FIG. 6, the pieces 600 can be connected together by a connecting member 612 extending through each of the pieces 600. The connecting member 612 preferably comprises an elongated member as a flexible wire, strand, fiber or thread. Alternatively, the connecting member can comprise an elongated substantially rigid post or shaft. By using one or more flexible members to connect the pieces 600 together, a stent having significant flexibility is produced.

Figure 7:
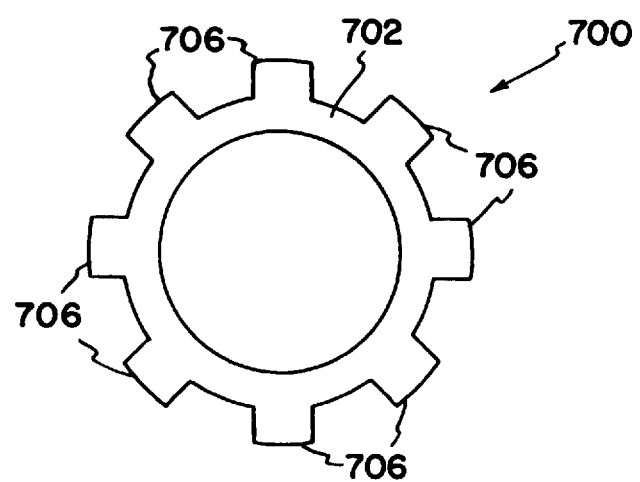
FIG. 7 shows an alternative cross-sectional piece suitable for use in accordance with the principles of the present invention, the piece includes a plurality of outer radial projections.

FIG. 7 shows another alternative annular piece 700 suitable for use with a method of the present invention. The piece 700 includes a solid inner portion 702 defining a central aperture 704. A plurality of outer radial projections 706 are spaced about the circumference of the inner portion 702.

In practicing a method for manufacturing a tubular medical device, such as a stent, the pieces 700 are cut from a substantially flat sheet of biocompatible material. The pieces 700 are then aligned on a support device such that the pieces 700 define an elongated tubular structure. Once the pieces 700 are aligned, the pieces are connected together by a technique such as diffusion bonding. After the pieces 700 have been fused together, the inner portion 702 is removed, preferably by a machining process, and the interconnected radial projections 706 are left as a remainder. The remaining projections 706 form the body, including interconnected struts and cross-members, of a tubular medical device such as a stent.

With regard to the foregoing description, it is to be understood that changes may be made in detail, especially in matters of the construction materials employed and the shape, size, and arrangement of the parts without departing from the scope of the present invention. It is intended that the specification and depicted embodiment be considered exemplary only, with a true scope and spirit of the invention being indicated by the broad meaning of the following claims.

What is claimed is:

1. A method for manufacturing a tubular medical device for insertion in a body, the method comprising the steps of:
   providing a sheet of biocompatible material;
   cutting a plurality of pieces from the sheet, the pieces defining apertures;
   aligning the pieces generally along an axis such that the pieces are arranged to form an elongated structure having an interior lumen extending longitudinally therethrough; and
   connecting the aligned pieces of the elongated structure together, wherein each of the interconnected pieces forms a layer of the elongated tubular medical device.

2. The method of claim 1, wherein the pieces are connected by fusing the pieces together.

3. The method of claim 1, wherein the pieces are connected by diffusion bonding.

4. The method of claim 1, wherein the pieces are connected by a connecting member extending longitudinally through each of the pieces.

5. The method of claim 4, wherein the connecting member comprises a flexible member.

6. The method of claim 5, wherein the flexible member comprises a flexible wire.

7. The method of claim 1, wherein each piece is substantially annular and includes a first surface positioned opposite from a second surface, the first and second surfaces defining a plurality of recesses configured to form lateral openings in the tubular medical device.

8. The method of claim 7, wherein the pieces are connected by a connecting member extending through each of the pieces.

9. The method of claim 1, wherein the pieces include circumferentially spaced radial projections.

10. The method of claim 9, wherein the projections comprise inner radial projections extending radially into the apertures of the pieces, and the method further comprises the step of removing an exterior portion of the elongated structure such that only the inner radial projections are left as a remainder.

11. The method of claim 10, wherein the exterior portion of the elongated structure is removed by a machining process.

12. The method of claim 10, wherein the inner radial projections have varying cross-sectional dimensions.

13. The method of claim 9, wherein the projections comprise outer radial projections extending radially outward from the elongated structure, and the method further comprises the step of removing an interior portion of the elongated structure such that only the outer radial projections are left as a remainder.

14. The method of claim 13, wherein the interior portion of the elongated structure is removed by a machining process.

15. The method of claim 13, wherein the outer radial projections have varying cross-sectional dimensions.

16. The method of claim 1, wherein the sheet is substantially flat.

17. The method of claim 1, wherein the biocompatible material is stainless steel.

18. The method of claim 1, wherein the tubular medical device comprises a stent.

19. The method of claim 1, wherein the pieces are connected by adhesive bonding.

20. A method for manufacturing a stent comprising the steps of:
    providing a sheet of biocompatible material;
    cutting a plurality of pieces from the sheet, the pieces defining apertures and including radial portions extending radially into the apertures, the radial portions defining void spaces located between the radial portions;
    aligning the pieces generally along an axis such that the pieces are arranged to form an elongated structure having an interior lumen extending longitudinally therethrough, the elongated structure having an outer boundary, an inner boundary, and an intermediate boundary located between the outer and inner boundaries, the radial portions being located between the inner boundary and the intermediate boundary;
    connecting the aligned pieces together; and
    removing an exterior portion of the elongated structure such that only the radial portions of the elongated member remain, wherein the remaining radial portions form a tubular stent body, and the void spaces between the radial portions form lateral openings in the stent body.

21. The method of claim 20, wherein the pieces are connected by fusing the pieces together.

22. The method of claim 20, wherein the pieces are connected by diffusion bonding.

23. The method of claim 20, wherein the exterior portion of the elongated structure is removed by a machining process.

* * * * *